United States Patent
Tu et al.

Patent Number: 6,053,913
Date of Patent: Apr. 25, 2000

[54] RAPID EXCHANGE STENTED BALLOON CATHETER HAVING ABLATION CAPABILITIES

[76] Inventors: Lily Chen Tu; Hosheng Tu, both of 2151 Palermo, Tustin, Calif. 92782

[21] Appl. No.: 09/150,182

[22] Filed: Sep. 10, 1998

[51] Int. Cl.$^7$ .................................................. A61B 18/18
[52] U.S. Cl. ........................... 606/41; 606/192; 606/193; 606/194; 604/96; 604/99; 600/585; 607/102; 607/122
[58] Field of Search ................................ 606/91, 46, 47, 606/27, 29, 31, 191, 194, 198; 607/96, 99, 113, 101; 604/96, 99, 104, 114, 529

[56] References Cited

U.S. PATENT DOCUMENTS

| | | | |
|---|---|---|---|
| 4,824,435 | 4/1989 | Giesy et al. | 604/49 |
| 5,078,736 | 1/1992 | Behl | 606/41 |
| 5,690,642 | 11/1997 | Osborne et al. | 606/108 |
| 5,695,498 | 12/1997 | Tower | 606/108 |
| 5,735,869 | 4/1998 | Fernandez-Aceytuno | 606/194 |
| 5,792,144 | 8/1998 | Fischell et al. | 606/108 |
| 5,860,974 | 1/1999 | Abele | 606/41 |
| 5,972,026 | 10/1999 | Laufer et al. | 607/96 |
| 5,980,484 | 11/1999 | Ressemann et al. | 604/96 |

OTHER PUBLICATIONS

G. Spera, "The Next Wave in Minimally Invasive Surgery" MD & DI pp. 36–44 Aug. 1998 published by Canon Communications.

*Primary Examiner*—Linda C. M. Dvorak
*Assistant Examiner*—David Ruddy

[57] ABSTRACT

An ablation apparatus for treating tissues or atherosclerosis on a patient having a prior angioplasty procedure, the ablation apparatus comprising a rapid exchange stented balloon catheter having a reversibly collapsible stent secured around the balloon and RF energy applied through the deployed stent to the tissue underlying the stent for therapeutic ablation purposes.

5 Claims, 3 Drawing Sheets

RAPID EXCHANGE STENTED BALLOON CATHETER HAVING ABLATION CAPABILITIES

TECHNICAL FIELD OF THE INVENTION

The present invention generally relates to improved medical apparatus and methods for treating vascular tissues, and more particularly, to a rapid exchange balloon catheter comprising at least one reversibly collapsible stent having RF ablation capabilities.

BACKGROUND OF THE INVENTION

An artery is one of the tube-shaped blood vessels that carries blood away from the heart to the body's tissues and organs. An artery is made up of an outer fibrous layer, a smooth muscle layer, a connecting tissue layer, and the inner lining cells. If arterial walls become hardened due to the accumulation of fatty substances, then blood flow can be diminished. Hardening of the arteries, or loss of vessel elasticity, is termed arteriosclerosis while fatty deposit build-up is termed atherosclerosis. Atherosclerosis and its complications are a major cause of death in the United States. Heart and brain diseases are often the direct result of this accumulation of fatty substances that impair the arteries' ability to nourish vital body organs.

The use of balloon catheters to treat stenosis or narrowing within various parts of the human body is well known. Balloon angioplasty is a nonsurgical method of clearing coronary and other arteries, blocked by atherosclerotic plaque, fibrous and fatty deposits on the walls of arteries. A catheter with a balloon-like tip is threaded up from the arm or groin through the artery until it reaches the blocked area. The balloon is then inflated, flattening the plaque and increasing the diameter of the blood vessel opening. The arterial passage is thus widened. As a result of enlarging the hardened plaque, cracks and lesions may unfortunately occur within the plaque to expose the underlying fresh tissue or denuded cells to the blood stream.

In a typical procedure, for example, to dilate a stenosis in the coronary arteries, a relatively large guiding catheter is inserted into the patient's arterial system in the groin. The guiding catheter is then advanced through the arteries to a location near the patient's heart. A small wire guide is then inserted into the guiding catheter and advanced to the distal end of the guiding catheter, at which point it is steered to extend through the stenosis in the coronary arteries. A balloon catheter is then advanced over the wire guide until the deflated balloon lies across the stenosis. A working fluid is then pumped through the balloon catheter, thereby inflating the balloon and dilating the passage through the stenosis.

There are limitations, however, to this technique's application, depending on the extent of the disease, the blood flow through the artery, and the part of the anatomy and the particular vessels involved. Plaque build-up and/or severe re-stenosis recurs within 6 months is up to 40–50 percent of those treated. Balloon angioplasty can only be characterized as a moderate-success procedure. Recently, a newer technique of inserting a metallic stenting element is used to permanently maintain the walls of the vessel treated at its extended opening state. Stents are tiny mesh tubes made of stainless steel or other metals and are used by heart surgeons to prop open the weak inner walls of diseased arteries. They are often used in conjunction with balloon angioplasty to prevent restenosis after the clogged arteries are treated. Stenting technique reduces the probability of restenosis, however, the success rate is still sub-optimal. The underlying fresh tissue or denuded cells still pose as a precursor for vessel reclosures or stenosis due to unknown reasons.

When a clogged artery is widened, the plaque is broken up and the underlying collagen or damaged endothelium is exposed to the blood flow. Collagen and/or damaged endothelium has a pro-thrombotic property that is part of body's healing process. Unless the collagen or the damaged endothelium is passivated or modulated, the chance for blood vessel clotting as well as restenosis always exists. Moderate heat is known to tighten and shrink the collagen tissue as illustrated in U.S. Pat. No. 5,456,662 and U.S. Pat. No. 5,546,954. It is also clinically verified that thermal energy is capable of denaturing the tissue and modulating the collagenous molecules in such a way that treated tissue becomes more resilient ("The Next Wave in Minimally Invasive Surgery" MD&DI pp. 36–44, August 1998). Therefore, it becomes imperative to post-treat vessels walls after the walls are treated with angioplasty and/or stenting procedures.

One method of reducing the size of cellular tissues in situ has been used in the treatment of many diseases, or as an adjunct to surgical removal procedures. This method applies appropriate heat to the tissues, and causes them to shrink and tighten. It can be performed on a minimal invasive fashion, which is often less traumatic than surgical procedures and may be the only alternative method, wherein other procedures are unsafe or ineffective. Ablative treatment apparatus have an advantage because of the use of a therapeutic energy that is rapidly dissipated and reduced to a nondestructive level by conduction and convection, to other natural processes.

RF therapeutic protocol has been proven to be highly effective when used by electrophysiologists for the treatment of tachycardia; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. Radiofrequency treatment, which exposes a patient to minimal side effects and risks, is generally performed after first locating the tissue sites for treatment. Radiofrequency energy, when coupled with a temperature control mechanism, can be supplied precisely to the apparatus-to-tissues contact site to obtain the desired temperature for treating a tissue.

A metallic stenting element deployed within a vessel, such as a coronary stent, has excellent metal-to-tissue contact surface. It becomes an ideal medium for applying thermal energy to the tissue needed for treatment or modulation. In the case of angioplasty alone, the enlarged blood vessel still needs certain metallic contact surface for delivering the RF thermal energy to the denuded collagen or damaged endothelium. A temporary metallic stenting element on a rapid exchange balloon catheter by connecting to a RF current is useful in this case to shrink and tighten the target tissue. A stented catheter is defined as a catheter that comprises a reversibly collapsible stent securely wrapped around the balloon of said catheter.

There is therefore a need in the prior art for a stented catheter that may be used with the same wire guide that is used to steer the balloon angioplasty catheter. The present invention is directed toward meeting this need for using the radiofrequency energy to treat a diseased artery or other tissues, such as esophagus, larynx, uterus, urethra and the like.

SUMMARY OF THE INVENTION

In general, it is an object of the present invention to provide a method and an improved medical ablation apparatus for generating heat, to treat the atherosclerosis, vascular vessels, or other tissues, such as intestine, bile ducts, colon, ureter, uterine tubes, and the like. It is another object of this invention to provide a method and an apparatus for treating atherosclerosis, vascular walls, or tubular cellular tissues in a patient by applying RF current to a reversibly collapsible stent on a stented catheter and consequently to the underlying tissues.

It is a further object of the present invention to relate a rapid exchange stented balloon catheter that allows exchange from a balloon angioplasty catheter to a stented catheter without the need to replace the angioplasty catheter wire guide with an exchange-length wire guide before exchanging the catheters. A stented catheter of the present invention is a catheter that comprises a reversibly collapsible stent securely wrapped around the balloon of said catheter. The collapsible stent is deployed along with the inflation of the balloon. Similarly, the collapsible stent is pre-shaped so that it collapses or retracts along with deflation of the balloon. The stented catheter includes a relatively short wire guide shaft that is bonded to the catheter shaft only at a location distal to the inflation lumen.

In one embodiment, a rapid exchange stented balloon catheter comprises a catheter shaft defining an inflation lumen, the inflation lumen having a proximal end and a distal end; an inflatable balloon having a proximal end and a distal end; a wire guide shaft defining a wire guide lumen, the wire guide having a proximal end and a distal end; and a catheter tip having a proximal end and a distal end; wherein the distal end of the inflation lumen opens into and is in fluid communication with an interior of the inflatable balloon, the distal end of the inflatable balloon is sealed by the proximal end of the catheter tip, said coupling being completely distal of the distal end of the inflatable balloon.

After such a dilatation procedure, a stented balloon catheter rapidly exchanges the dilatation balloon catheter, wherein the collapsible stent on the stented catheter is connected through an electrical conductor to an external RF generator. The collapsible stent is securely and firmly wrapped around the deflated balloon of the stented catheter and the catheter is inserted into the patient's body to the location of the stenosis. When the balloon of the stented catheter is inflated, the collapsible stent is deformed to an expanded condition to contact the inner wall of the vascular vessel. An external RF generator is provided to supply RF current to the expanded stent to effect the RF ablation. After completing ablation therapy, the balloon is deflated and the stent is reversibly collapsed. The stented catheter is withdrawn from the body.

In another embodiment, a stented balloon catheter comprises a catheter shaft defining an inflation lumen having a proximal end and a distal end; a wire guide shaft defining a wire guide lumen, said wire guide shaft having a distal end and a proximal end; a catheter tip having a proximal end and a distal end; and a reversibly collapsible stent securely and firmly wrapped around said inflatable balloon and wire guide shaft; wherein the distal end of the inflation lumen opens into and is in fluid communication with the inflatable balloon, the distal end of the inflatable balloon is sealed by the proximal end of the catheter tip, and the wire guide shaft is coupled to the catheter tip, said coupling being completely distal of the distal end of the inflatable balloon. In an additional embodiment, a RF current is provided through an electrical conductor to the reversibly collapsible stent for RF therapy purposes.

For illustration purposes of a rapid exchange balloon catheter procedure, in a typical balloon angioplasty procedure, after the stenosis has been dilated, the balloon angioplasty catheter and wire guide are removed from the guiding catheter and a second wire guide, or exchange wire guide, is inserted through the guiding catheter and steered to the stenosis location. The exchange wire guide is more than twice as long as the stented catheter because it is necessary that the wire guide protrudes from the patient's body by a length greater than the length of the stented catheter. This allows the exchange wire guide to be held steady with the physician's hand while the stented catheter is advanced over the exchange guide wire. Once the distal end of the stented catheter has been placed within the area of the dilated stenosis, the balloon of the stented catheter may be inflated, thereby temporarily deforming the stent in the region of the dilated stenosis. RF current is then provided to the stent for therapeutic purposes. The balloon of the stented catheter is deflated, allowing the stented catheter along with the collapsed stent to be withdrawn. The exchange wire guide and the guiding catheter are then withdrawn, thereby completing the operation.

In principles, heat is generated by supplying a suitable energy source to a stented balloon catheter, which is comprised of at least one reversibly collapsible stent, in contact with the body tissues through a stented catheter. Examples for the reversibly collapsible stents include coronary stent, peripheral stent, uterine stent and the like. A suitable energy source may consist of radiofrequency energy, microwave energy, ultrasonic energy, alternating current energy, or laser energy. The energy can be applied to the stent and consequently to the atherosclerosis, vascular walls, or cellular tissues. A DIP (dispersive indifferent pad) type pad or electrode, that contacts the patient, is connected to the Indifferent Electrode Connector on the RF generator. Therefore, the RF energy delivery becomes effective when a close circuit from a RF generator through a patient and returning to the RF generator is formed. When using an alternating current outlet, the generator should be grounded to avoid electrical interference. Heat is controlled by the power of the RF current delivered and by the delivery duration. The standard RF current generator means and its applications through a metallic electrode means, to a patient are well known for those who are skilled in the art.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Figure 1:
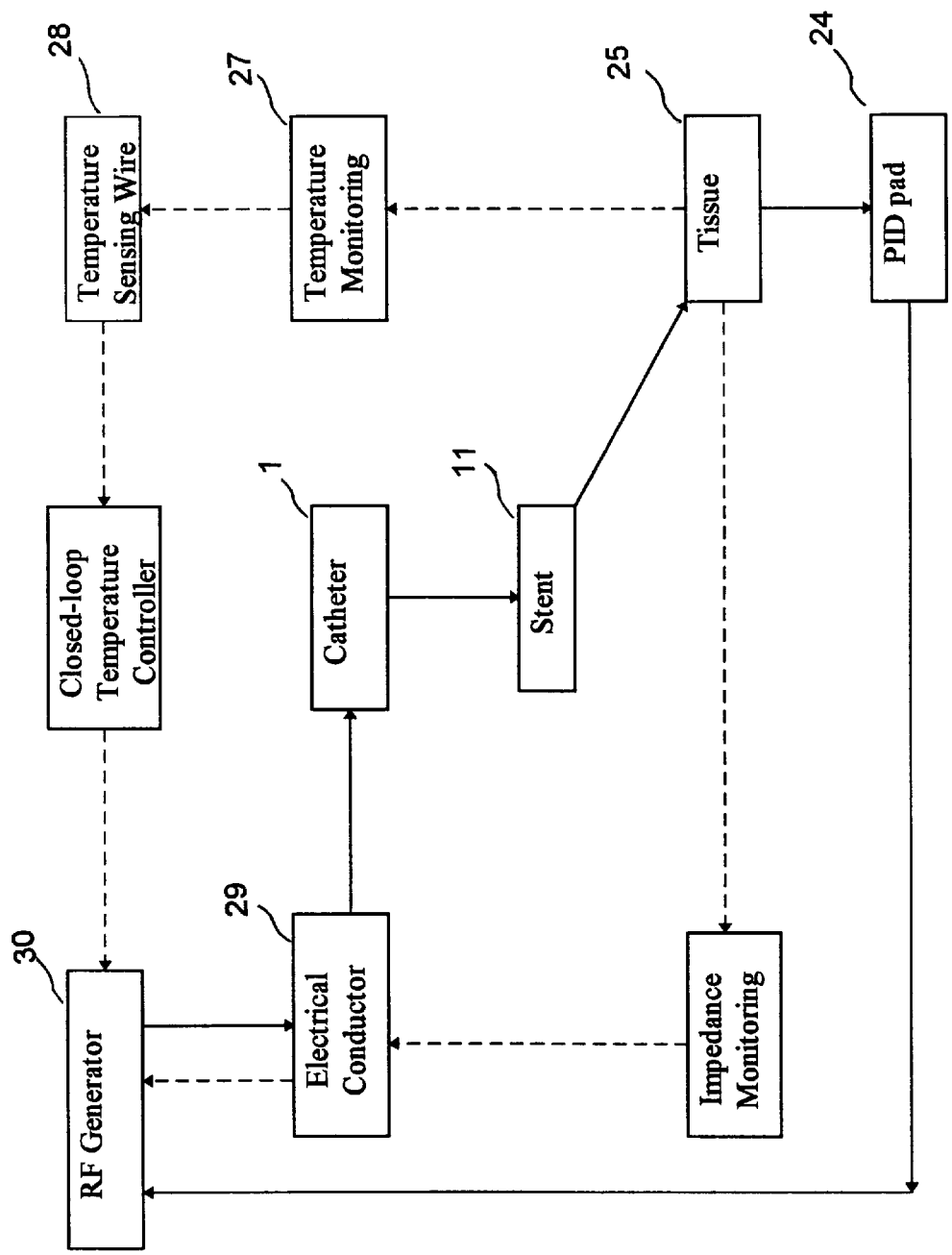
FIG. 1 is a schematic diagram of a RF treatment method in relation to the tissues or atherosclerosis through a reversibly collapsible stent of a stented catheter.
Figure 2:
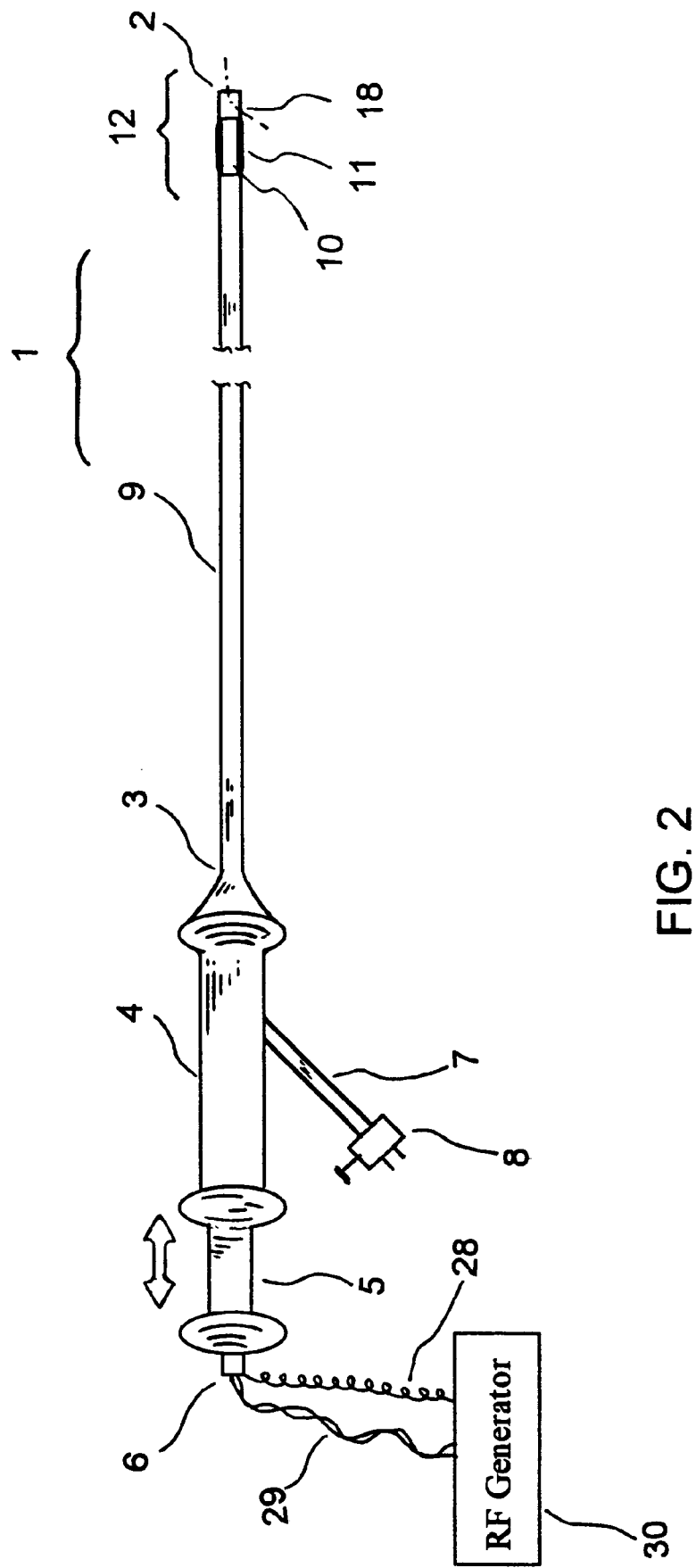
FIG. 2 is an overall view of a stented balloon catheter having a deployable balloon, a reversibly collapsible stent, and a RF generator, constructed in accordance to the principles of the present invention.
Figure 3:
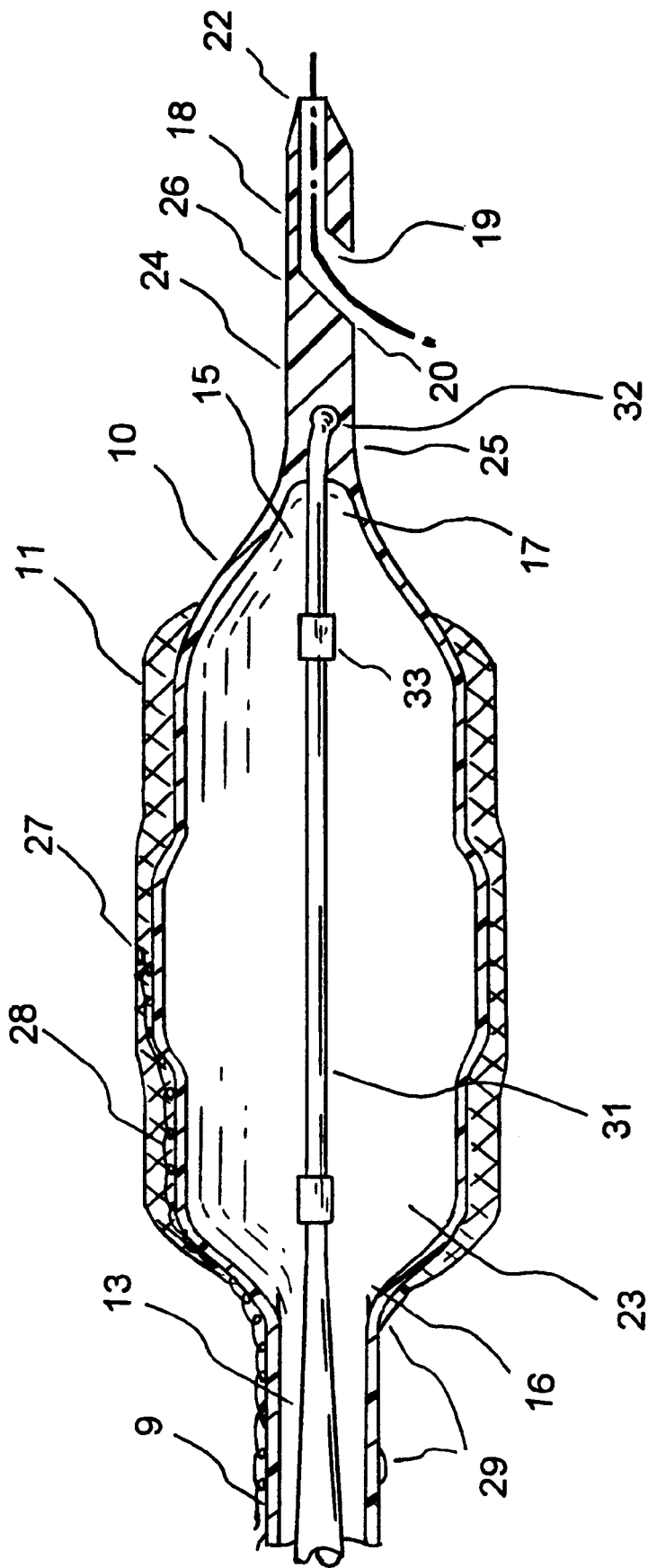
FIG. 3 is a cross-sectional view of the distal end portion of the stented balloon catheter, having a rapid exchange mechanism, a deployed stent on the inflated balloon, at a deployed state.

Referring to FIGS. 1 to 3, what is shown is an embodiment of the rapid exchange stented balloon catheter system, comprising applying radiofrequency energy therapy to treat the atherosclerosis, vascular vessels, or other tubular cellular tissues of a patient through a deployed reversibly collapsible stent securely wrapped around the balloon of a stented catheter.

FIG. 1 shows a schematic diagram of a RF treatment method in relation to the tissues or atherosclerosis through a deployed metallic stent in a patient. A RF generator 30 is connected to a catheter 1 through an electrical conductor 29. A deployed balloon of the catheter 1 is to expand the reversibly collapsible stent 11 when the catheter is in a deployed state. The stent is in close contact with the underlying tissue 25. A DIP (dispersive indifferent pad) type pad 24 that contacts the patient, is connected to the Indifferent Electrode Connector on the RF generator 30. Therefore, the RF current delivery becomes effective when a close circuit from a RF generator through a patient and returning to the RF generator is formed. Impedance measured from the tissue contact is to ensure good tissue contact for ablation, otherwise the RF power is cutoff when the impedance exceeds a pre-determined value. A temperature sensor 27 is optionally used to measure the tissue temperature and is relayed through a temperature sensing wire 28 to a closed-loop temperature controller for controlling the ablative current delivered. Heat is controlled by the power of the RF energy delivered and by the delivery duration. The temperature for tissue modulation is generally in the range of 60–80° C.

FIG. 2 shows an overall view of a stented balloon catheter having a deployable balloon 10, a reversibly collapsible stent 11, and a RF generator 30, constructed in accordance to the principles of the present invention. The stented balloon catheter system in the form of an elongate tubular assembly comprises a catheter shaft 9 having a distal section 12, a distal end 2, a proximal end 3, and at least one lumen 13 extending therebetween, wherein the at least one lumen has at least one opening at the distal section 12 of the catheter shaft 9. A handle or connecting means 4 is attached to the proximal end 3 of the catheter shaft 9, wherein the handle 4 has a cavity. A hollow tubing 7 having a proximal end, a distal end, a passageway and a locking valve 8 is attached to the handle 4, wherein the passageway is connected to the at least one lumen 13 of the catheter shaft 9. In an alternate embodiment, the proximal end of the hollow tubing 7 preferably terminates with a standard female lure type fitting (not shown) for attachment to a syringe for inflation and deflation of the inflatable balloon 10.

As shown in FIG. 3, a rapid exchange stented balloon catheter system comprises a catheter shaft 9 defining an inflation lumen 13, wherein the inflation lumen has a proximal end and a distal end 15. The inflation lumen 13 extends far enough in the proximal direction (not shown) in order to allow the proximal end of the catheter shaft 9 to be outside of the patient's body when the inflatable balloon 10 is placed across the stenosis. An inflatable balloon 10 has a proximal end 16 and a distal end 17.

A wire guide shaft 18 defines a wire guide lumen 19, the wire guide shaft having an open proximal end 20 and an open distal end 22 in order to allow a wire guide to pass therethrough, wherein the proximal end of the wire guide shaft is distal to the distal end 17 of the inflatable balloon 10. The proximal end 20 of the wire guide shaft 18 is formed at an angle to a transverse axis of the wire guide shaft 18. This reduces the chance of damage to the vessel wall as the catheter 1 is withdrawn.

A reversibly collapsible stent 11 is securely and firmly wrapped around said inflatable balloon 10, wherein an electrical conductor 29 is connected to said stent 11. A catheter tip 24 has proximal end 25 and distal end 26, wherein the distal end 15 of the inflation lumen 13 opens into and is in communication with an interior 23 of the inflatable balloon 10, the distal end 17 of the inflatable balloon 10 is sealed by the proximal end 25 of the catheter tip 24, and the wire guide shaft 18 is coupled only to the catheter tip completely distally of the distal end 17 of the inflatable balloon 10. The distal end 17 of the inflatable balloon 10 is closed and merges into the catheter tip 24.

A stiffening wire 31 extends through the inflation lumen 13 and the interior of the inflatable balloon 10 and terminates within the catheter tip 24. The stiffening wire 31 preferably includes a small ball or other enlargement 32 at its distal end in order to anchor the stiffening wire 31 within the catheter tip 24. The stiffening wire is preferably formed from stainless steel or Nitinol shape-memory superelastic material. At least one radiopaque marker band 33 is placed around the stiffening wire 31 near the proximal end 16 or the distal end 17 of the inflation balloon 10. The radiopaque marker band 33 may be made of any radiopaque material, such as gold, tungsten, silver or platinum. The location of the at least one radiopaque marker band 33 allows the position of the inflatable balloon 10 to be accurately determined by fluoroscopy in order to ensure proper positioning of the inflatable balloon prior to inflation.

The external RF generator 30 (shown in FIG. 2) is part of the balloon catheter system, wherein RF current is provided through the electrical conductor 29 to the reversibly collapsible stent 11. The RF current is preferably in the range of 50 kHz to 2,000 kHz.

The stented balloon catheter 1 is preferably formed from at least one of the following material: polyethylene, cross-linked polyethylene, polypropylene, polyimide, polyethylene terephthalate, and nylon. Reversibly collapsible stents of various types are able to grip and secure to a folded or deflated polyethylene or other types of balloon well.

The stented catheter of the present invention can be used to deploy balloon-expanded stents in several parts of the anatomy for further ablation therapy, and is not limited solely to the location of coronary arteries. For coronary arteries, the balloon diameter and consequently the reversibly collapsible stent diameter is generally in the range of 1.5 to 5 mm while the balloon length is generally 10 to 30 mm. The overall length of the catheter should be around 110 cm or longer and the stiffening wire should be approximately 0.010–0.015 inches in diameter. The distal end of the stiffening wire can be tapered in order to allow more flexibility at the distal end of the catheter shaft 9. The outside diameter of the catheter shaft 9 should be approximately 0.7 to 2.0 mm.

The stented balloon catheter is preferably formed by starting with a length of tubing which is equal in cross-sectional dimensions to the desired dimensions of the catheter shaft 9. The distal end of this tubing is closed and a portion of the tubing is placed into a mold which has the shape and dimensions of the desired size of the inflated balloon 10. The section of the tubing within the mold is then heated and the interior of the tubing is pressurized such that the portion of the tubing within the mold expands to the interior dimensions of the mold. The tubing is then cooled such that the material within the mold retains the shape of the interior of the mold. The mold is then removed and the distal end of the tubing is cut distal to the distal end of the balloon at the desired distance. This will allow a portion of the distal end become the catheter tip 17. During molding, a stiffening wire 31, having at least one radiopaque marker band 33, can be inserted inside the lumen all the way to the distal end 25 of the tubing so that the distal ball 32 is partially molded into the distal end of the catheter shaft 9. In one embodiment, the balloon has a variable diameter inflation profile for firmly securing the reversibly collapsible stent in place.

A second section of tubing having dimensions desired for the wire guide shaft 18 is then placed next to the catheter tip 24 such that the proximal end 20 of the wire guide shaft 18 is adjacent the distal end 26 of the catheter tip 24.

In one embodiment, at least one temperature sensing means 27 is disposed at close proximity of the deployed reversibly collapsible stent 11. Insulated temperature sensor wire means 28 passes from the temperature sensing means 27, to an external temperature control mechanism through an outlet connector 6. The RF current delivery is controlled by using the measured temperature from the temperature sensing means 27, through a closed-loop temperature control mechanism and/or algorithm. When the measured temperature rises to a preset high-limit point, the temperature control mechanism sends out a signal to cut off the RF current supply. In a similar manner, when the measured temperature drops to a preset low-limit point, the temperature control mechanism sends out a signal to activate the RF current supply.

Alternatively, a stented catheter system comprising a catheter shaft 9 having a distal section 12, proximal and distal ends, and at least one lumen extending therebetween. A reversibly collapsible stent 11 is firmly secured around the distal section of the catheter shaft, wherein an electrical conductor is connected to the stent. Means for extending and retracting the reversibly collapsible stent radially is provided, wherein means for extending and retracting the stent radially may include a zig-zag type wire or mesh mechanism, mechanical means, electromechanical means, or a shape-memory Nitinol design. The catheter system further comprises a RF current generator means 30, wherein RF current is provided through the electrical conductor 29 to the reversibly collapsible stent 11. Optionally, the stented catheter system further comprising an inflatable balloon mounted on the distal section of the catheter shaft, wherein the inflatable balloon has proximal and distal ends; an inflation lumen on the catheter shaft, wherein the inflation lumen has proximal and distal ends; and a catheter tip 24 having proximal and distal ends, wherein the distal end of the inflation lumen opens into and is in communication with an interior of the inflatable balloon, the distal end of the inflatable balloon 10 is sealed by the proximal end of the catheter tip 24.

For illustration purposes, a method of inserting a stented balloon catheter of the catheter system into a patient's body for treating stenosis, the method comprising: inserting the stented balloon catheter at a non-deployed state into the patient's body to the location of stenosis; deploying the inflatable balloon; providing RF current to the reversibly collapsible stent; un-deploying the inflatable balloon; and withdrawing the stented balloon catheter from the patient's body.

The external RF current generator means has the capability to supply RF current by controlling the time, power, and temperature through an optionally separate closed-loop temperature control means. The patient is connected to the RF generator means through a DIP electrode to form a closed-loop circuit system. Therefore, RF current is applied and delivered to the targeted atherosclerosis region, through the deployed stent of this invention. The radiofrequency energy current in this invention is preferably within the range of 50 to 2,000 kHz. By simultaneously applying RF energy to the deployed stent and by applying the pressure against the underlying tissues by the deployed stent, the tissues can be treated.

In a particular embodiment, the material for the stent of this invention consists of conductive metals such as platinum, iridium, gold, silver, stainless steel, Nitinol, or an alloy of these metals.

From the foregoing description, it should now be appreciated that an ablation catheter system for the tubular organs, atherosclerosis, and the treatment of vascular tissues, comprising a suitable energy therapy has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A rapid exchange stented balloon catheter system comprising:

a catheter shaft defining an inflation lumen, the inflation lumen having a proximal and distal ends;

an inflatable balloon having proximal and distal ends;

a wire guide shaft having proximal and distal ends defining a wire guide lumen having an open proximal end and an open distal end, wherein the proximal end of the wire guide shaft is distal to the distal end of the inflatable balloon and wherein the proximal end of the wire guide shaft is formed at an angle to a transverse axis of the wire guide shaft;

a reversibly collapsible stent made of a nitinol material formed in a mesh type ziz-zag configuration securely and firmly wrapped around said inflatable balloon, wherein an electrical conductor is connected to the stent;

said inflatable balloon having a variable diameter inflation profile for firmly securing the reversibly collapsible stent in place;

a catheter tip having proximal and distal ends, wherein the distal end of the inflation lumen opens into and is in communication with an interior of the inflatable balloon, the distal end of the inflatable balloon is sealed by the proximal end of the catheter tip, and the wire guide shaft is coupled only to the catheter tip completely distally of the distal end of the inflatable balloon;

a stiffening wire made of nitinol shape memory material, having a proximal end and a tapered distal end for providing increased flexibility at the distal end, wherein the stiffening wire extends through the interior of the inflation lumen and terminates within the catheter tip, the stiffening wire including a small ball at the distal end for anchoring the stiffening wire within the catheter tip;

at least one radiopaque marker band coupled to the stiffening wire for marking a location of at least one end of the inflatable balloon;

an external closed-loop temperature controller and a temperature sensor disposed near a midpoint along the length of the reversibly collapsible stent, the temperature sensor being connected to an external closed-loop temperature controller by means of an insulated temperature sensor wire which extends in a proximal direction from the temperature sensor;

said temperature sensor being adapted to sense and relay temperature to the controller; and a RF generator, wherein RF current is provided through the electrical conductor to the reversibly collapsible stent.

2. The stented balloon catheter system of claim 1, wherein the RF current is in the range of 50 kHz to 2,000 kHz.

3. The stented balloon catheter system of claim 1, wherein the reversibly collapsible stent is made of material selected from the group of stainless steel, gold, silver, platinum, iridium and Nitinol.

4. The stented balloon catheter system of claim 1, wherein the balloon is made of material selected from the group consisting of polyethylene, cross-linked polyethylene, polyethylene terephthalate, and nylon.

5. A method of inserting a stented balloon catheter system into a patient's body for treating stenosis, the catheter comprising a catheter shaft defining an inflation lumen, the inflation lumen having proximal and distal ends; an inflatable balloon having proximal and distal ends; a wire guide shaft having proximal and distal ends defining a wire guide lumen, the wire guide shaft having an open proximal end and an open distal end, wherein the proximal end of the wire guide shaft is distal to the distal end of the inflatable balloon and wherein the proximal end of the wire guide shaft is formed at an angle to a transverse axis of the wire guide shaft;

a reversibly collapsible stent made of a nitinol material formed in a mesh type ziz-zag configuration securely and firmly wrapped around said inflatable balloon, wherein an electrical conductor is connected to the stent;

said inflatable balloon having a variable diameter inflation profile for firmly securing the reversibly collapsible stent in place;

a catheter tip having proximal and distal ends, wherein the distal end of the inflation lumen opens into and is in communication with an interior of the inflatable balloon, the distal end of the inflatable balloon is sealed by the proximal end of the catheter tip, and the wire guide shaft is coupled only to the catheter tip completely distally of the distal end of the inflatable balloon;

a stiffening wire made of nitinol shape memory material, having a proximal end and a tapered distal end for providing increased flexibility at the distal end, wherein the stiffening wire extends through the interior of the inflation lumen and terminates within the catheter tip, the stiffening wire including a small ball at the distal end for anchoring the stiffening wire within the catheter tip;

at least one radiopaque marker band coupled to the stiffening wire for marking a location of at least one end of the inflatable balloon;

an external closed-loop temperature controller and a temperature sensor disposed near a midpoint along the length of the reversibly collapsible stent, the temperature sensor being connected to an external closed-loop temperature controller by means of an insulated temperature sensor wire which extends in a proximal direction from the temperature sensor;

said temperature sensor being adapted to sense and relay temperature to the controller;

and a RF generator, wherein RF current is provided through the electrical conductor to the reversibly collapsible stent;

the method comprising:
  inserting the stented balloon catheter at a non-deployed state into the patient's body to the location of stenosis;
  inflating the inflatable balloon;
  providing RF current to the reversibly collapsible stent in order to treat a patient's stenosis;
  deflating the inflatable balloon; and
  withdrawing the stented balloon catheter from the patient's body.

\* \* \* \* \*